United States Patent [19]

Krahnke et al.

[11] Patent Number: 5,017,672

[45] Date of Patent: May 21, 1991

[54] POLYALKOXYSILYLALKYLENEDISILA-ZANES AND SILYLAMINES

[75] Inventors: Robert H. Krahnke; John C. Saam, both of Midland, Mich.

[73] Assignee: Dow Corning Corporation, Midland, Mich.

[21] Appl. No.: 306,136

[22] Filed: Feb. 6, 1989

Related U.S. Application Data

[62] Division of Ser. No. 95,962, Sep. 11, 1987, Pat. No. 4,847,400.

[51] Int. Cl.$^5$ .............................................. C08G 77/08
[52] U.S. Cl. ...................................... 528/23; 528/12; 528/33; 528/34
[58] Field of Search ....................... 528/12, 23, 33, 34, 528/38

[56] References Cited

U.S. PATENT DOCUMENTS

| | | | |
|---|---|---|---|
| 4,448,927 | 5/1984 | Falender et al. | 524/860 |
| 4,652,624 | 3/1987 | Allen et al. | 528/17 |
| 4,683,277 | 7/1987 | Maxson | 528/21 |
| 4,722,987 | 2/1988 | Ikeno et al. | 528/23 |
| 4,725,643 | 2/1988 | Burkhardt | 528/23 |
| 4,835,237 | 5/1989 | Burkhardt et al. | 528/21 |

Primary Examiner—John C. Bleutge
Assistant Examiner—R. Dean, Jr.
Attorney, Agent, or Firm—Edward C. Elliott

[57] ABSTRACT

A polyalkoxysilylalkylenedisilazane of the formula

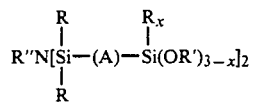

and a polyalkoxysilylalkylenesilylamine of the formula

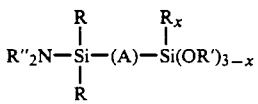

where x is 0 or 1; R is a saturated alkyl or aryl radical or mixture of radicals; R' is alkyl, aryl, or Cellosolve (R) alkylethanol radical, or mixture of radicals; R'' is hydrogen, alkyl, aryl, or aryalkyl radial or mixture of radicals; and A is a divalent hydrocarbon radical having 2 to 20 carbon atoms; and a method for their manufacture by the platinum catalyzed addition of an alkenyl-functional disilazane or silylamine with an alkoxy-functional silicon hydride is disclosed. The silylamine can also be produced by the platinum catalyzed addition of a SiH functional silazane or silylamine and an alkenyltrialkoxysilane. The polyalkoxysilylalkylenedisilanzane and the polyalkoxysilylalklylenesilylamine can be reacted with a silanol containing polyorganosiloxane such as a hydroxyl endblocked polydiorganosiloxane in the presence of an acidic catalyst to give a polyalkoxysilyl terminated polydiorganosiloxane in which the terminal groups are bonded to the polymer through an alkylene linkage.

6 Claims, No Drawings

POLYALKOXYSILYLALKYLENEDISILAZANES AND SILYLAMINES

This is a divisional of co-pending application Ser. No. 07/095,962 filed on Sept. 11, 1987, now U.S. Pat. No. 4,847,400.

BACKGROUND OF THE INVENTION

1. Field of the Invention

This invention relates to polyalkoxysilylalkylenedisilazanes and polyalkoxysilylalkylenesilylamines and their use to produce polyalkoxysilyl terminated polydiorganosiloxanes in which the terminal group is bonded to the polymer through an alkylene linkage.

2. Background Information

U.S. Pat. No. 3,175,993, issued Mar. 30, 1965 teaches organopolysiloxanes which are endblocked with alkoxylated silcarbane groups. The compositions are prepared by reacting a hydrogen endblocked siloxane with an alkoxylated aliphatic silane in the presence of a platinum catalyst, or by reacting an aliphatic endblocked siloxane with an alkoxylated silane in the presence of a platinum catalyst. The use of the product in producing sealants is also taught.

U.S. Pat. No. 4,395,526 issued July 26 1983 teaches one package moisture curable polyalkoxy-terminated organopolysiloxane compositions having a condensation catalyst. The composition can be made using a silanol terminated polydiorganosiloxane and a silane scavenger. U.S. Pat. No. 4,515,932, issued May 7, 1985 teaches a novel end-capping catalyst for such materials.

West German Pat. No. 3,524,484, issued July 7, 1985, teaches the condensation of linear organopolysiloxanes containing SiOH groups in the presence of phosphorus nitride chloride catalyst, and the reaction with hexaorganodisilazane to give an organopolysiloxane with triorganosiloxy end groups.

U.S. Pat. No. 4,599,394, issued Jul 8, 1986 teaches reacting a silanol-terminated polydiorganosiloxane or vinyl-terminated polydiorganosiloxane with a hydrogen-containing polyalkoxysilane in the presence of a platinum catalyst. The resulting alkoxy-terminated polydiorganosiloxane can be used to produce RTV silicone rubber compositions.

A method of producing silicone elastomeric sealants of the type using a polyalkoxy-terminated polymer, crosslinker, and titanium catalyst with improved shelf life is taught in U.S. Pat. No. 4,652,624. issued Mar. 24, 1987. The shelf life is improved by adding a polyalkoxy-terminated polymer which has the terminal silicon bonded to the next silicon through a divalent hydrocarbon radical.

SUMMARY OF THE INVENTION

A polyalkoxysilylalkylenedisilazane of the formula

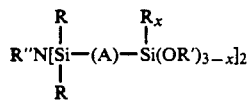

or a polyalkoxysilylalkylenesilylamine of the formula

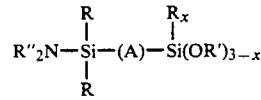

where x is 0 or 1; R is a saturated alkyl or, aryl radical or mixture of radicals; R' is alkyl, aryl, or cellosolve (R) 2-alkylethanol radical, or mixture of radicals; R" is hydrogen, alkyl, aryl, or arylalkyl radical or mixture of radicals; and A is a divalent hydrocarbon radical having 2 to 20 carbon atoms is produced by the platinum catalyzed addition of an alkenyl-functional disilazane or silylamine with an alkoxy-functional silicon hydride. The silylamine can also be produced by the platinum catalyzed addition of a SiH functional silazane or silylamine and an alkenyltrialkoxysilane. The polyalkoxysilylalkylenedisilazane and the polyalkoxysilylalkylenesilylamine can be reacted with a hydroxyl endblocked polydiorganosiloxane in the presence of an acidic catalyst to give a polyalkoxysilyl terminated polydiorganosiloxane in which the terminal groups are bonded to the polymer through an alkylene linkage.

DESCRIPTION OF THE INVENTION

This invention relates to a polyalkoxysilylalkylenedisilazane of the formula

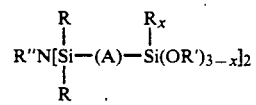

where x is 0 or 1; R is a saturated alkyl or aryl radical, or mixture thereof; R' is alkyl, aryl, or cellosolve (R) 2-alkylethanol radical, or mixture thereof; R" is hydrogen, alkyl, aryl, or arylalkyl radical or mixture thereof; and A is a divalent hydrocarbon radical having 2 to 20 carbon atoms. R can be any monovalent hydrocarbon radical free of aliphatic unsaturation such as alkyl radicals such as methyl, ethyl, isopropyl, octadecyl or myricyl; cycloaliphatic hydrocarbon radicals such as cyclopentyl, cyclohexyl or methylcyclohexyl; aryl hydrocarbon radicals such as phenyl, xenyl, tolyl, naphthyl or anthrancyl, aralkyl hydrocarbon radicals such as benzyl, 2-phenylethyl, or 2-phenylpropyl, and substituted hydrocarbon radicals such as 3,3,3-trifluoropropyl. R' includes the radicals of R plus cellosolve (R) 2-alkylethanol radicals. R" includes the radicals of R plus arylalkyl radicals and hydrogen. A is a divalent hydrocarbon radical such as —(CH$_2$)$_2$—, —(CH$_3$)CH—, —CH$_2$CH$_2$ O CH$_2$CH$_2$—, —CH$_2$(CH$_3$)CHCH$_2$—, —(CH$_2$)$_6$—, —(CH$_3$)CH O (CH$_3$)CH—, and —CH$_2$CH$_2$ O —(CH$_3$)CH—. A also includes variations of a divalent hydrocarbon radical such as a radical containing hetero group or atom such as oxygen or ether in the chain, the hetero group or atom being at least 2 or more carbon atoms removed from the silicon atom, such as —CH$_2$CH$_2$CH$_2$OCH$_2$CH$_2$— and —(CH$_3$)CHCH$_2$O(CH$_3$)CHCH$_2$—.

This invention also relates to a polyalkoxysilylalkylenesilylamine of the formula

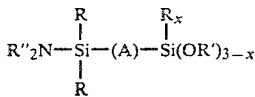

where x is 0 or 1; R is a saturated alkyl or aryl radical, or mixture thereof; R' is alkyl, aryl, or cellosolve (R) 2-alkylethanol or mixture thereof; R" is hydrogen, alkyl, aryl, or arylalkyl radical or mixture thereof; and A is a divalent hydrocarbon radical having 2 to 20 carbon atoms.

These compositions are used in a method for preparing a polyalkoxysilyl containing polyorganosiloxane in which the polyalkoxysilyl are bonded to the polymer through an alkylene linkage, the method comprising (A) mixing in the absence of moisture, (1) hydroxyl endblocked polydiorganosiloxane, (2) the polyalkoxysilylalkylenedisilazane or the polyalkoxysilylalkylenesilylamine described above, and (3) acidic catalyst where the molar amount of (2) is in excess of the molar amount of (1), and (B) allowing the mixture to react until the hydroxyl groups have been replaced with polyalkoxysilylalkyl groups.

The method of this invention can also be used to add a polyalkoxysilylalkylene radical to any material containing the required SiOH group to complete the reaction. The necessary OH group can also be in the form of a carbonol functional group or a phenolic group, such as the novalac resins.

Methods of making polyalkoxysilyl terminated polydiorganosiloxane in which the terminal group is bonded to the polymer through an alkylene link are known, as shown in U.S. Pat. No. 3.175.993. The reactions taught involve the use of a platinum catalyst. Because the activity of a platinum catalyst may be easily poisoned by contaminants, in practice it can easily result in a polymer that is not properly reacted and therefore may not cure properly when used in a sealant formulation. In a production situation this might not be known until the compounded sealant was tested.

It has been found that when a polyalkoxysilyl terminated polydiorganosiloxane in which the terminal group is bonded to the polymer through an alkylene link is compounded into a sealant formulation through the use of a trialkoxyalkylsilane and a titanate catalyst, the formulation has an outstanding shelf life as compared to a formulation in which the polymer used is a polyalkoxysilyl terminated polydiorganosiloxane in which the terminal group is bonded to the next silicon through an oxygen link. Whether the intended polymer is present is sometimes not known until the sealant is tested after a long storage period, at which time the product may be in the hands of potential users. Because the sealant fails by not curing, the failure is particularly expensive because then the sealant must be removed from the location where it was placed as a seal before it can be replaced.

The method of this invention reacts an alkoxyfunctional silicon hydride with an alkenyl-functional disilazane or silylamine in the presence of a platinum catalyst. This reaction is easily monitored by standard gas chromatography to insure that the reaction has taken place and the desired product is produced. A polyalkoxysilyl terminated polydiorganosiloxane in which the terminal group is bonded to the polymer through an alkylene link is then produced by reacting the polyalkoxysilylalkylenedisilazane or polyalkoxysilylalkylenesilylamine with a hydroxyl endblocked polydiorganosiloxane in the presence of an acid catalyst. This reaction is much less susceptible to inhibition than the platinum catalyzed reaction.

The polyalkoxysilylalkylenedisilazane of the formula

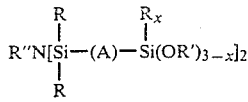

is typically produced by mixing 2 moles of polyalkoxysilane of the formula

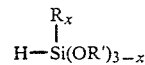

with 1 mole of dialkylalkenyldisilazane of the formula

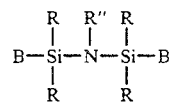

in the presence of a platinum catalyst. In these formulas x is 0 or 1: R is a saturated alkyl, aryl radical, or mixture thereof; R' is alkyl, aryl, cellosolve (R) 2-alkylethanol radical, or mixture thereof; R" is hydrogen, alkyl, aryl, or arylalkyl radical or mixture thereof; and B is a monovalent hydrocarbenyl radical having 2 to 20 carbon atoms or monovalent hydrocarbenyl ether radical. The reaction is best carried out by mixing the disilazane with the platinum catalyst and heating to greater than 70° C., followed by the addition of the polyalkoxysilane. After an initiation period, the temperature of the reaction can be easily controlled by the rate of addition of the polyalkoxysilane. The preferred temperature is in the range of 20° C. to 130° C., with a range of from 70° C. to 130° C. most preferred. The reaction product can be used as is or it can be purified by vacuum distillation. B is a monovalent hydrocarbenyl radical having from 2 to 20 carbon atoms such as — CH=CH$_2$, —(CH$_3$)C=CH$_2$,

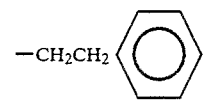

—CH$_2$—(CH$_3$)C=CH$_2$, —(CH$_2$)$_4$CH=CH$_2$, and

B also includes variations of a divalent hydrocarbenyl radical such as a radical containing hetero group or atom such as oxygen or ether in the chain, the hetero group or atom being at least 2 or more carbon atoms removed from the silicon atom, such as —CH$_2$CH$_2$CH$_2$OCH=CH$_2$ and —(CH$_3$)CHCH$_2$OCH=CH$_2$.

The preferred alkenyl radical is the vinyl radical.

A polyalkoxysilylalkylenesilylamine of the formula

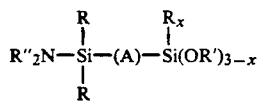

can be produced by the same procedure with the substitution of a dialkylalkenylsilazane of the formula

for the disilazane used above. In this process only 1 mole of the polyalkoxysilane is used.

A polyalkoxysilyl containing polyorganosiloxane in which the polyalkoxysilyl groups are bonded to the polymer through an alkylene linkage can be produced by mixing, in the absence of moisture, a silanol containing polyorganosiloxane, the polyalkoxysilylalkylenedisilazane or the polyalkoxysilylalkylenesilylamine of this invention and acidic catalyst and allowing the mixture to react until the silanol groups have been replaced with polyalkoxysilylalkylsilyl groups. A slight molar excess of the disilazane or silylamine over the silanol in the polymer is preferred to insure complete reaction with all of the silanols and any water that may be in the system.

A polyalkoxy terminated polydiorganosiloxane in which the terminal groups are bonded to the polymer through an alkylene linkage can be produced by mixing in the absence of moisture, hydroxyl endblocked polydiorganosiloxane, the polyalkoxysilylalkylenedisilazane or the polyalkoxysilylalkylenesilylamine of this invention and acidic catalyst and allowing the mixture to react until the hydroxyl endblocking has been replaced with polyalkoxysilylalkylsilyl endblocking. A slight molar excess of the disilazane over the silanol in the polymer is preferred to insure complete reaction with all of the silanols and any water that may be in the system. Excess, unreacted disilazane or silylamine is not expected to be detrimental to the subsequent sealant composition. The rate at which the reaction occurs depends upon the temperature, the type of catalyst and the concentration of catalyst. Preferably, the temperature is between 15° C. and 100° C. although the reaction will go below and above these limits. If too high a temperature is used, the mixture may become highly colored due to decomposition products from the disilazane. Catalysts include acetic acid, trifluoroacetic acid, phosphoric acid, trifluoromethane sulfonic acid, xylenesulfonic acid and dodecylbenzenesulfonic acid. Trifluoroacetic acid and dodecylbenzenesulfonic acid are preferred because they are active enough for the reaction to be carried out at lower temperatures and acid concentrations. Trifluoromethane sulfonic acid is probably too strong and results in some siloxane rearrangement. The concentration of the catalyst can vary widely and is determined by the specific temperature and rate requirements selected for the process.

The usefulness of these polymers in producing sealants which will cure on exposure to moisture and which do not give off any corrosive byproducts was shown by comparing such formulations to similar commercial compositions which are made using a hydroxyl endblocked polymer instead of the polymer produced by the method of this invention.

When a composition consisting essentially of a hydroxyl endblocked polymer, an alkyltrialkoxysilane crosslinker, filler, and a chelated titanium catalyst is mixed in the absence of moisture, a sealant results which will cure upon exposure to moisture. The alkyltrialkoxysilane reacts with the hydroxyl endblocked polymer to give an alkyldialkoxysilyl endblocked polymer when the composition is mixed. In the presence of a chelated titanium catalyst, such a mixture will cure to an elastomer upon exposure to moisture. It has now been found that such compositions undergo other reactions upon long time storage under normal storage conditions in sealed containers at room temperature. These reactions can be accelerated by storage for shorter periods of time at elevated temperatures. Two weeks at 70° C. correlates to about 1 year at room temperature. Upon such storage, the compositions loose their ability to cure upon exposure to moisture. The durometer of the sealant upon curing gradually lowers and the elongation raises until the sealant no longer cures to a useful product. This type of failure is particularly bad because it is not apparent until the sealant has been put in place and left to cure. After such a failure is discovered, it is necessary to remove all of the uncured sealant before it can be replaced with newly manufactured sealant which will cure properly. Such a replacement is, of course, very expensive.

When a similar sealant composition is made, but substituting a polymer containing a polyalkoxysilyl terminal group attached to the polymer through an alkylene linkage such a loss of curability upon storage does not occur.

A test comparing the two types of compositions showed that the composition prepared with the common hydroxyl endblocked polymer lost its curability in 7 days at 70° C., while the composition using the polymer prepared as taught in this invention was essentially unchanged. The test results were as follows:

|  | This Invention | Comparative |
|---|---|---|
| Durometer |  |  |
| Initial | 41 | 38 |
| 2 days | 40 | 20 |
| 4 days | 40 | 19 |
| 7 days | 43 | 11 |
| 100% Modulus |  |  |
| Initial | 202 | 85 |
| 2 days | 220 | 70 |
| 4 days | 230 | 65 |
| 7 days | 220 | 25 |

While the polyalkoxy terminated polydiorganosiloxanes produced by the method of this invention are most useful in curable compositions using a chelated titanium catayst as is illustrated above, the polydiorganosiloxanes can also be used with other cure systems which are known in the art, for example with tin catalysts.

The following examples are included for illustrative purposes only and should not be construed as limiting the invention which is properly set forth in the appended claims. All parts are parts by weight. In the examples, Me is methyl radical, Et is ethyl radical, Vi is vinyl radical, Cl is chlorine radical, and Ac is acetate radical.

EXAMPLE 1

A polyalkoxysilylalkylenedisilazane was prepared at room temperature by adding 3.28g (20 mmoles) of triethoxysilane, (EtO)₃SiH, to 1.85g (10mmoles) of dimethylvinyldisilazane, Me₂ViSiNHSIMe₂Vi, in the presence of 2 drops of chloroplatinic acid complex of divinyltetramethyldisiloxane diluted with dimethylvinylsiloxy endblocked polydimethylsiloxane to provide 0.7 weight percent platinum. After about 5 minutes, a vigorous exotherm occurred and within 15 minutes, the reaction was complete. The product was analyzed by gas chromatography and found to be primarily a triethoxysilylethylene(dimethyl)disilazane in which the silicon atoms were bonded by an ethylene linkage of the formula

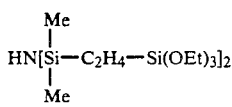

To determine how well this disilazane would silylate a silanol-ended polymer, a mixture was prepared containing 0.159g (0.51 mmoles) of a dimethyltrisiloxane having a methyl endblocking group on one end and a hydroxyl endblock on the other end, 0.132g (0.26 mmoles) of the above disilazane, and a trace of trifluoroacetic acid catalyst. After ½ hour the reaction product was analyzed by gas chromatography and found to be essentially of the formula

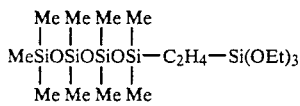

where Me is methyl radical.

EXAMPLE 2

In a three-neck round bottom flask was combined 46.5g (0.27 moles) of dimethylvinyldisilazane and 0.72g of the platinum catalyst used in example 1. After heating to 70° C., 89.0g (0.54 moles of triethoxysilane was added over a period of 45 minutes at 70° to 100° C. External heat was applied over the next 90 minute period to maintain the temperature at 100° C. The product was analyzed and found to be 87 percent of the desired triethoxysilyl endblocked disilazane having an ethylene linkage between the silicon on the end and the silicon on the nitrogen as shown in Example 1. The reaction product was distilled to purify the product.

EXAMPLE 3

A mixture was prepared of 1000.0g of a hydroxyl endblocked polydimethylsiloxane having a molecular weight of about 15000 (131.2 mmoles of hydroxyl) and 31.30 g (61.0 mmoles) of the disilazane of example 2. To this was added 3.39g (10.4 mmoles) of dodecylbenzenesulfonic acid, then the mixture was allowed to react for tWo days at room temperature. The original viscosity of the silanol-ended polymer was 14,000 cps and after endcapping, the viscosity remained at 14,000 cps.

Sealant bases were prepared by hand mixing the filler shown in Table I with the endcapped polymer prepared above and then giving two passes through a two roll mill. The bases were then placed in sealant cartridges and catalyzed by adding a mixture of methyltrimethoxysilane and organotitanate catalyst, as shown in Table I, and mixing for 5 minutes at room temperature in the absence of moisture. The organotitinate catalyst was 2,5-di-isopropoxy-bis-ethylacetoacetate titanium. After standing for 1 week at room temperature to allow the mixture to come to equilibrium, test sheets were prepared and allowed to cure for 1 week at 70° C. and 45 percent relative humidity. The sealant cartridges were placed in an oven at 70° C. and aged with test sheets prepared after 2, 4, and 7 days oven aging. The results of testing the various sheets are shown in Table I.

The skin over time is defined as the time required for the material to cure to the point where it no longer adheres to a clean fingertip lightly applied to the surface. The cure conditions are 23° C. and 50 percent relative humidity. The tack free time is defined as the time in minutes required for a curing material to form a non-tacky surface film. A sample is spread on a clean smooth surface and timing is begun. Periodically, a cleand strip of polyethylene film is layed upon a fresh surface and a one ounce weight applied to it. After 4 seconds, the weight is removed and the strip gently pulled off. The time when the strip pulls cleanly away from the sample is recorded as the tack free time.

Durometer is measured in accordance with ASTM D-2240, tensile strength and elongation are measured in accordance with ASTM D-412.

TABLE I

|  | E7394-010A | E7394-010B |
| --- | --- | --- |
| Formulations | A | B |
| Polymer, parts | 100 | 100 |
| Filler, parts |  |  |
| calcium carbonate, parts | 90 |  |
| fume silica, parts |  | 10 |
| Methyltrimethoxysilane, parts | 4 | 4 |
| Titanate catalyst, parts | 2 | 2 |

| Aging | Skin Over Time minutes | Tack Free Time minutes | Durometer Shore A | Tensile Strength psi | Elongation percent |
| --- | --- | --- | --- | --- | --- |
| Sample A |  |  |  |  |  |
| 1 wk/RT | 20 | 38 | 42 | 252 | 181 |
| 2 day/70° C. | 19 | 39 | 40 | 265 | 162 |
| 4 day/70° C. | 25 | 34 | 40 | 296 | 202 |
| 1 wk/70° C. | 16 | 20 | 43 | 304 | 252 |
| 2 wk/70° C. | — | 14 | 39 | 286 | 264 |
| Sample B |  |  |  |  |  |

TABLE I-continued

| | | | | | |
|---|---|---|---|---|---|
| 1 wk/RT | 15 | 30 | 34 | 300 | 242 |
| 2 day/70° C. | 19 | 39 | 30 | 285 | 221 |
| 4 day/70° C. | >34 | 54 | 30 | 429 | 273 |
| 1 wk/70° C. | — | >76 | 30 | 403 | 252 |
| 2 wk/70° C. | 27 | 50 | 30 | 297 | 220 |

EXAMPLE 4

A variety of acid catalysts were evaluated for their usefulness in catalyzing the reaction between a hydroxyl endblocked polydimethylsiloxane and the disilazane of example 2.

A mixture was prepared of 4.51g (0.10 moles hydroxyl) of a hydroxyl endblocked polydimethylsiloxane having a molecular weight of 900 and 2.71g (0.10 moles) of the disilazane of Example 2 and varying amounts of different acid catalysts as shown in Table II. The mixtures were allowed to react at room temperature or 100C as shown. Samples were analyzed periodically by gas chromatography. The extent of reaction is shown by the formation of the reaction products $HO(Me_2SiO)_4H$ (xD4x) and $HO(Me_2SiO)_6H$ (xD6x). The results are shown in Table II.

the reactor over a period of time from 20 minutes to 1200 minutes. As each 100g sample was withdrawn, further reaction was stopped by adding 2 parts of methyltrimethoxysilane crosslinker and 1 part of tetraisopropoxytitanate catalyst to each sample. A part of each sample was immediately laid out to cure by exposure to the moisture in the air. Another part of each sample was placed into an oven heated to 70° C. for 2 weeks of accelerated aging and then laid out to cure.

After each sample had cured for 2 weeks, the plasticity was measured, using the procedure of ASTM D-926, with the result shown in Table III.

TABLE III

| Reaction Time | Initial | Plasticity Number After Oven Aging |
|---|---|---|
| 20 minutes | 790 | 400 |
| 40 | 840 | 470 |

TABLE II

| Sample | Catalyst | Amount ppm | Reaction Time/Temp | Percent Theory xD4x | Percent Theory xD6x |
|---|---|---|---|---|---|
| A | F$_3$CCOOH | 22222 | 2 hr/RT | 39 | 28 |
| B | F$_3$CCOOH | 19500 | 10 min/100° C. | 100 | 100 |
| C | F$_3$CCOOH | 1930 | 10 min/100° C. | 100 | 100 |
| D | F$_3$CCOOH | 210 | 10 min/100° C. | 76 | 73 |
| | | | 40 min/100° C. | 100 | 100 |
| E | H$_3$PO$_4$ | 1930 | 3 hr/100° C. | 3 | 3 |
| | | | 24 hr/100° C. | 11 | 115 |
| F | ClSiMe$_2$Vi | 2897 | 10 min/100° C. | 0 | 0 |
| | | | 3 day/100° C. | 62 | 57 |
| | | | 4 day/100° C. | 16 | 21 |
| G | DBSA* | 2904 | 5 min/100° C. | 56 | 54 |
| | | | 10 min/100° C. | 88 | 83 |
| | | | 20 min/100° C. | 100 | 99 |
| H | DBSA* | 4406 | 30 min/RT | 9 | 9 |
| | | | 1 hr/RT | 17 | 17 |
| | | | 2 hr/RT | 24 | 24 |
| | | | 3 hr/RT | 32 | 33 |
| | | | 5 hr/RT | 41 | 41 |
| I | HOAc | 1381 | 2 hr/100° C. | 0 | 0 |
| | | | 24 hr/100° C. | 53 | 60 |
| L | HOAc | 1526 | 10 min/RT | 0 | 0 |
| | | | 20 min/RT | 0 | 0 |
| | | | 90 min/RT | 3 | 2 |
| | | | 3 hr/RT | 5 | 5 |
| | | | 7 hr/RT | 10 | 11 |
| | | | 3 day/RT | 50 | 55 |
| M | F$_3$CSO$_3$H | 200 | 5 hr/RT | 17 | 21 |
| | | | 3 day/RT | 50 | 56 |
| | | | 60 min/100° C. | 80 | 82 |
| | | | 3 hr/100° C. | 97 | 97 |

*Dodecylbenzenesulfonic acid

EXAMPLE 5

First 1485 parts of a hydroxyl endblocked polydimethylsiloxane having a viscosity of 12 Pa.s at 25° C. was added to a reactor and 42.5 parts of a disilazane of the formula

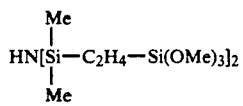

was added along with 200 parts per million of trifluoroacetic acid. Samples were periodically removed from

| | | |
|---|---|---|
| 64 | 860 | 480 |
| 100 | 900 | 640 |
| 167 | 960 | 790 |
| 1200 | 1020 | 980 |

The increasing plasticity of the initial samples shows that as the hydroxyl ends of the polymer were replaced by the multifunctional trimethoxysilyl ends from the disilazane reaction, there is a greater crosslink density. Comparing the plasticity loss on aging between the initial sample and the sample with the accelerated oven aging shows that as the polymer ends were changed to the trimethoxysilylethylene ends, the polymer become more resistant to the effects of the oven aging. The polymer which had been reacted for 1200 minutes was essentially unchanged by the oven aging as shown by the maintenance of the initial plasticity.

That which is claimed is:

1. A method for preparing a polyalkoxysilyl containing polyorganosiloxane in which the polyalkoxysilyl groups are bonded to the polymer through an alkylene linkage comprising (A) mixing in the absence of moisture,
  (1) silanol containing polyorganosiloxane,
  (2) a polyalkoxysilylalkylenedisilazane of the formula

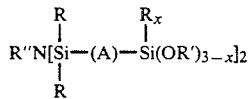

where x is 0 or 1; R is a saturated alkyl or aryl radical, or mixture thereof; R' is alkyl, aryl, or Cellosolve (R) 2-alkylethanol radical, or mixture thereof; R" is hydrogen, alkyl, aryl, or arylalkyl radical or mixture thereof; and A is a divalent hydrocarbon radical having 2 to 20 carbon atoms, and
  (3) acidic catalyst, where the molar amount of (2) is in excess of the molar amount of (1), and (B) allowing the mixture to react until the silanol groups have been replaced with polyalkoxysilylalkylsilyl groups.

2. The method of claim 1 in which the silanol containing polyorganosiloxane is a hydroxyl endblocked polydiorganosiloxane.

3. The method of claim 1 in which the reaction temperature is from 15° C., the acidic catalyst is trifluoroacetic acid or dodecylbenzenesulfonic acid, and R and R' are methyl or ethyl radicals.

4. The method of claim 1 in which R" is hydrogen.

5. The method of claim 4 in which the silanol containing polyorganosiloxane is a hydroxyl endblocked polydiorgansiloxane.

6. The method of claim 4 in which the reaction temperature is from 15° C. to 100° C., the acidic catalyst is trifluoroacetic acid or dodecylbenzenesulfonic acid, R and R' are methyl or ethyl radicals and R" is hydrogen.

* * * * *